(12) United States Patent
Lee et al.

(10) Patent No.: US 7,709,237 B2
(45) Date of Patent: May 4, 2010

(54) CRYSTAL STRUCTURE OF CMY-10, A β-LACTAMASE CAUSING ANTIBIOTIC RESISTANCE WITH EXTENDED-SUBSTRATE SPECTRUM

(75) Inventors: Sang-Hee Lee, Gyonggiy-do (KR); Sun-Shin Cha, Gyongsangbuk-do (KR); Jung-Hun Lee, Seoul (KR); Ha-Il Jung, Daejeon (KR)

(73) Assignee: Myongji University Industry and Academia Cooperation

( * ) Notice: Subject to any disclaimer, the term of this patent is extended or adjusted under 35 U.S.C. 154(b) by 24 days.

(21) Appl. No.: 11/659,244

(22) PCT Filed: Jul. 25, 2005

(86) PCT No.: PCT/KR2005/002400
§ 371 (c)(1),
(2), (4) Date: Oct. 10, 2008

(87) PCT Pub. No.: WO2006/011736
PCT Pub. Date: Feb. 2, 2006

(65) Prior Publication Data
US 2009/0061421 A1 Mar. 5, 2009

(30) Foreign Application Priority Data
Jul. 26, 2004 (KR) .................. 10-2004-0058283
May 17, 2005 (KR) .................. 10-2005-0041342

(51) Int. Cl.
*C12N 9/00* (2006.01)
*C12N 9/14* (2006.01)
*C12N 9/78* (2006.01)
*C12N 9/86* (2006.01)
*C07K 14/00* (2006.01)
*C07K 17/00* (2006.01)

(52) U.S. Cl. .................. 435/183; 435/195; 435/227; 435/231; 530/350

(58) Field of Classification Search .................. None
See application file for complete search history.

(56) References Cited

OTHER PUBLICATIONS

Crichlow et al. (Structure of the Extended-Spectrum Class C β-Lactamase of Enterobacter cloacae GC1, a Natural Mutant with a Tandem Tripeptide Insertion\, Biochemistry, 1999, 38 (32), 10256-10261).*

Kim et al. (Structural basis for the extended substrate spectrum of CMY-10, a plasmid-encoded class C β-lactamase, Molecular Microbiology (2006), 60 (4), 907-916).*

GenBank: ACO24915.1, class C beta-lactamase CMY-10, Retrieved from the Internet <URL: http://www.ncbi.nlm.nih.gov/protein/ACO24915?ordinalpos=1&itool=EntrezSystem2.PEntrez.Sequence.Sequence_ResultsPanel.Sequence_RVDocSum), Retrieved on Sep. 28, 2009.*

Sun-Joo Lee, et al.; "Crystallization and preliminary X-ray crystallographic analyses of CMY-1 and CMY-10, plasmidic class C beta-lactamases with extended substrate spectrum", In: acta Crystallographica; Feb. 2, 2004; D60; pp. 382-384.

* cited by examiner

*Primary Examiner*—Suzanne M. Noakes
*Assistant Examiner*—Jae W Lee
(74) *Attorney, Agent, or Firm*—Edwards Angell Palmer & Dodge LLP; Kongsik Kim

(57) ABSTRACT

The present invention related to a method for crystallizing a CMY-10 being a β-lactamase with extended-substrate spectrum, a crystal of CMY-10, and a crystal structure of CMY-10. With utilization of three-dimensional structure of CMY-10 protein provided by the present invention, it is possible to develop novel antibiotics or inhibitors that can prevent an emergence of resistance bacteria appeared by plasmidic class C β-lactamases having extended-substrate specificity.

1 Claim, 8 Drawing Sheets
(8 of 8 Drawing Sheet(s) Filed in Color)

CMY-10

SEQUENCE LISTING

<160> NUMBER OF SEQ ID NOS: 7

<210> SEQ ID NO 1
<211> LENGTH: 1475
<212> TYPE: DNA
<213> ORGANISM: Enterobacter aerogenes
<220> FEATURE:
<221> NAME/KEY: CDS
<222> LOCATION: (251)..(1396)

<400> SEQUENCE: 1

```
aacgagtgag ggaatttcag gtaagatact tcggatgagg agcaaaaagg tggtttatac      60
ttcctatacc cccagccgcc gggcaagggg gggcaagtca tggataaccc attgaaactg     120
ggctatttga acgccgactt cacatcggct tcacagagcc tcatattgcg cacaccttgc     180
gggattaggc tgggagcact gccaggcacc caggcagcac attcgactta tgacgagagg     240
agtagacccg atg caa caa cga caa tcc atc ctg tgg ggg gcc gtg gcc acc     292
            Met Gln Gln Arg Gln Ser Ile Leu Trp Gly Ala Val Ala Thr
              1               5                  10 ctg atg tgg gcc ggt ctg gcc cat gca ggt gag gct tca ccg gtc gat         340
Leu Met Trp Ala Gly Leu Ala His Ala Gly Glu Ala Ser Pro Val Asp
 15                  20                  25                  30 ccc ctg cgc ccc gtg gtg gat gcc agc atc cag ccg ctg ctc aag gag         388
Pro Leu Arg Pro Val Val Asp Ala Ser Ile Gln Pro Leu Leu Lys Glu
                 35                  40                  45 cac agg atc ccg ggc atg gcg gtg gcc gtg ctc aag gat ggc aag gcc         436
His Arg Ile Pro Gly Met Ala Val Ala Val Leu Lys Asp Gly Lys Ala
             50                  55                  60 cac tac ttc aat tac ggg gtg gcc aac cgg gag agc ggg gcc ggc gtc         484
His Tyr Phe Asn Tyr Gly Val Ala Asn Arg Glu Ser Gly Ala Gly Val
         65                  70                  75 agc gag cag acc ctg ttc gag ata gga tcc gtg agc aag acc ctg act         532
Ser Glu Gln Thr Leu Phe Glu Ile Gly Ser Val Ser Lys Thr Leu Thr
     80                  85                  90 gcg acc ctg ggg gcc tat gcg gtg gtc aag gga gcg atg cag ctg gat         580
Ala Thr Leu Gly Ala Tyr Ala Val Val Lys Gly Ala Met Gln Leu Asp
 95                 100                 105                 110 gac aag gcg agc cgg cac gcg ccc tgg ctc aag gga tcc gcc ttt gac         628
Asp Lys Ala Ser Arg His Ala Pro Trp Leu Lys Gly Ser Ala Phe Asp
                115                 120                 125 agc atc acc atg ggg gag ctt gcc acc tac agc gcc gga ggc ctg cca         676
Ser Ile Thr Met Gly Glu Leu Ala Thr Tyr Ser Ala Gly Gly Leu Pro
            130                 135                 140 ctg caa ttc ccc gag gag gtg gat tca tcc gag aag atg cgc gcc tac         724
Leu Gln Phe Pro Glu Glu Val Asp Ser Ser Glu Lys Met Arg Ala Tyr
        145                 150                 155 tac cgc cag tgg gcc cct gtc tat tcg ccg ggc tcc cat cgc cag tac         772
Tyr Arg Gln Trp Ala Pro Val Tyr Ser Pro Gly Ser His Arg Gln Tyr
    160                 165                 170 tcc aac ccc agc ata ggg ctg ttc ggc cac ctg gcg gcg agc agc ctg         820
Ser Asn Pro Ser Ile Gly Leu Phe Gly His Leu Ala Ala Ser Ser Leu
175                 180                 185                 190 aag cag ccg ttt gcc ccc ttg atg gag cag acc ctg ctg ccc ggg ctc         868
Lys Gln Pro Phe Ala Pro Leu Met Glu Gln Thr Leu Leu Pro Gly Leu
```

-continued

```
                195                 200                 205
ggc atg cac cac acc tat gtc aat gtg ccg aag cag gcc atg gcg agt        916
Gly Met His His Thr Tyr Val Asn Val Pro Lys Gln Ala Met Ala Ser
        210                 215                 220 tat gcc tat ggc tat tcg aaa gag gac aag ccc atc cgt gtc aac cct        964
Tyr Ala Tyr Gly Tyr Ser Lys Glu Asp Lys Pro Ile Arg Val Asn Pro
                225                 230                 235 ggc atg ctg gcg gac gag gcc tat ggc atc aag acc agc tcg gcg gat       1012
Gly Met Leu Ala Asp Glu Ala Tyr Gly Ile Lys Thr Ser Ser Ala Asp
    240                 245                 250 ctg ctg cgt ttt gtg aag gcc aac atc ggc ggg gtt gat gac aag gcg       1060
Leu Leu Arg Phe Val Lys Ala Asn Ile Gly Gly Val Asp Asp Lys Ala
255                 260                 265                 270 ttg cag cag gcc atc tcc ctg acc cac caa ggg cat tac tcg gta ggc       1108
Leu Gln Gln Ala Ile Ser Leu Thr His Gln Gly His Tyr Ser Val Gly
                275                 280                 285 ggg atg acc cag ggg ctg ggt tgg gag agt tac gcc tat ccc gtc acc       1156
Gly Met Thr Gln Gly Leu Gly Trp Glu Ser Tyr Ala Tyr Pro Val Thr
        290                 295                 300 gag cag aca ttg ctg gcg ggc aat tcg gcc aag gtg atc ctc gaa gcc       1204
Glu Gln Thr Leu Leu Ala Gly Asn Ser Ala Lys Val Ile Leu Glu Ala
                305                 310                 315 aat ccg acg gcg gcg ccc cgg gag tcg ggg agc cag gtg ctc ttc aac       1252
Asn Pro Thr Ala Ala Pro Arg Glu Ser Gly Ser Gln Val Leu Phe Asn
    320                 325                 330 aag acc ggc tcg acc aat ggc ttt ggc gcc tat gtg gcc ttc gtg ccg       1300
Lys Thr Gly Ser Thr Asn Gly Phe Gly Ala Tyr Val Ala Phe Val Pro
335                 340                 345                 350 gcc agg ggg atc ggc atc gtc atg ctg gcc aat cgc aac tac ccc atc       1348
Ala Arg Gly Ile Gly Ile Val Met Leu Ala Asn Arg Asn Tyr Pro Ile
                355                 360                 365 gag gcg cgc atc aag gcg gcc cac gcc atc ctg gcg cag ttg gcc ggt       1396
Glu Ala Arg Ile Lys Ala Ala His Ala Ile Leu Ala Gln Leu Ala Gly
        370                 375                 380 tgaa agaaagaggg cggtacattc ggtgaatgtg ccgccctttt tctggtgctg           1450
ggggaatacc cccgctagtc gtact                                           1475
```

<210> SEQ ID NO 2
<211> LENGTH: 382
<212> TYPE: PRT
<213> ORGANISM: Enterobacter aerogenes

<400> SEQUENCE: 2

```
Met Gln Gln Arg Gln Ser Ile Leu Trp Gly Ala Val Ala Thr Leu Met
  1               5                  10                  15

Trp Ala Gly Leu Ala His Ala Gly Glu Ala Ser Pro Val Asp Pro Leu
                 20                  25                  30

Arg Pro Val Val Asp Ala Ser Ile Gln Pro Leu Leu Lys Glu His Arg
             35                  40                  45

Ile Pro Gly Met Ala Val Ala Val Leu Lys Asp Gly Lys Ala His Tyr
         50                  55                  60

Phe Asn Tyr Gly Val Ala Asn Arg Glu Ser Gly Ala Gly Val Ser Glu
 65                  70                  75                  80

Gln Thr Leu Phe Glu Ile Gly Ser Val Ser Lys Thr Leu Thr Ala Thr
                 85                  90                  95

Leu Gly Ala Tyr Ala Val Val Lys Gly Ala Met Gln Leu Asp Asp Lys
            100                 105                 110
```

-continued

```
Ala Ser Arg His Ala Pro Trp Leu Lys Gly Ser Ala Phe Asp Ser Ile
    115                 120                 125

Thr Met Gly Glu Leu Ala Thr Tyr Ser Ala Gly Gly Leu Pro Leu Gln
130                 135                 140

Phe Pro Glu Glu Val Asp Ser Ser Glu Lys Met Arg Ala Tyr Tyr Arg
145                 150                 155                 160

Gln Trp Ala Pro Val Tyr Ser Pro Gly Ser His Arg Gln Tyr Ser Asn
                165                 170                 175

Pro Ser Ile Gly Leu Phe Gly His Leu Ala Ala Ser Ser Leu Lys Gln
            180                 185                 190

Pro Phe Ala Pro Leu Met Glu Gln Thr Leu Leu Pro Gly Leu Gly Met
        195                 200                 205

His His Thr Tyr Val Asn Val Pro Lys Gln Ala Met Ala Ser Tyr Ala
    210                 215                 220

Tyr Gly Tyr Ser Lys Glu Asp Lys Pro Ile Arg Val Asn Pro Gly Met
225                 230                 235                 240

Leu Ala Asp Glu Ala Tyr Gly Ile Lys Thr Ser Ser Ala Asp Leu Leu
                245                 250                 255

Arg Phe Val Lys Ala Asn Ile Gly Gly Val Asp Asp Lys Ala Leu Gln
            260                 265                 270

Gln Ala Ile Ser Leu Thr His Gln Gly His Tyr Ser Val Gly Gly Met
        275                 280                 285

Thr Gln Gly Leu Gly Trp Glu Ser Tyr Ala Tyr Pro Val Thr Glu Gln
    290                 295                 300

Thr Leu Leu Ala Gly Asn Ser Ala Lys Val Ile Leu Glu Ala Asn Pro
305                 310                 315                 320

Thr Ala Ala Pro Arg Glu Ser Gly Ser Gln Val Leu Phe Asn Lys Thr
                325                 330                 335

Gly Ser Thr Asn Gly Phe Gly Ala Tyr Val Ala Phe Val Pro Ala Arg
            340                 345                 350

Gly Ile Gly Ile Val Met Leu Ala Asn Arg Asn Tyr Pro Ile Glu Ala
        355                 360                 365

Arg Ile Lys Ala Ala His Ala Ile Leu Ala Gln Leu Ala Gly
    370                 375                 380

<210> SEQ ID NO 3
<211> LENGTH: 36
<212> TYPE: DNA
<213> ORGANISM: Artificial Sequence
<220> FEATURE:
<223> OTHER INFORMATION: N-NdeIF Primer

<400> SEQUENCE: 3
gtagaccata tgcaacaacg acaatccatc ctgtgg                              36

<210> SEQ ID NO 4
<211> LENGTH: 34
<212> TYPE: DNA
<213> ORGANISM: Artificial Sequence
<220> FEATURE:
<223> OTHER INFORMATION: N-NdeIF Primer

<400> SEQUENCE: 4
gaatgtctcg agctctttct ttcaaccggc caac                                34

<210> SEQ ID NO 5
<211> LENGTH: 22
<212> TYPE: DNA
```

-continued

```
<213> ORGANISM: Artificial Sequence
<220> FEATURE:
<223> OTHER INFORMATION: UP-26b-BglII Primer

<400> SEQUENCE: 5
ctatcatgcc atacccgcaa ag                                            22

<210> SEQ ID NO 6
<211> LENGTH: 60
<212> TYPE: DNA
<213> ORGANISM: Artificial Sequence
<220> FEATURE:
<223> OTHER INFORMATION: Sp-HIS Primer

<400> SEQUENCE: 6
gctatgatga tgatgatgat gatgatgatg atgatgatcc ggtgaagcct cacctgcatg   60

<210> SEQ ID NO 7
<211> LENGTH: 49
<212> TYPE: DNA
<213> ORGANISM: Artificial Sequence
<220> FEATURE:
<223> OTHER INFORMATION: EK-CMY Primer

<400> SEQUENCE: 7
agcggccata tcgacgacga cgacaagggt gaggcttcac cggtcgatc               49
```

CRYSTAL STRUCTURE OF CMY-10, A β-LACTAMASE CAUSING ANTIBIOTIC RESISTANCE WITH EXTENDED-SUBSTRATE SPECTRUM

CROSS-REFERENCES TO RELATED APPLICATIONS

This application is a U.S. national phase application, pursuant to 35 U.S.C. §371, of PCT international application Ser. No. PCT/KR2005/002400, filed Jul. 25, 2005, designating the United States and published in English on Feb. 2, 2006 as publication WO 2006/011736 A1, which claims priority to Korean Application No. 10-2004-0058283 filed on Jul. 26, 2004 and Korean Application No. 10-2005-0041342 filed on May 17, 2005. The entire contents of the aforementioned patent applications are incorporated herein by this reference.

TECHNICAL FIELD

The present invention relates to a crystal structure of CMY-10 from *Enterobacter aerogenes*, a β-lactamase of plasmid class C causing resistance for β-lactam antibiotics, more precisely to a method for crystallizing a CMY-10 being a β-lactamase with extended-substrate spectrum, a crystal of CMY-10, and a crystal structure of CMY-10.

BACKGROUND ART

β-Lactam antibiotic, including penicillins, cephalosporins, monobactams, and carbapenems induces a death of live cell by inhibition of cell-wall synthesis (Tomasz, 1979). But it is induced an emergence of bacteria having a resistance for the above β-lactam antibiotics due to a broad use of these antibiotics. Expression of β-lactamase is a general resistance mechanism of bacteria for β-lactam antibiotics, which these enzymes hydrolyze a lactam-ring of the above antibiotics. β-Lactamase is classified into four classes of A, B, C, and D according to homology of amino acid sequence (Ambler, 1980).

The β-lactamase-mediated resistance of pathogenic bacteria to antibiotics is a continuing threat to public health. Therefore, a third generation of cephalosporins was developed that could escape inactivation by β-lactamases. The new antibiotics such as cefotaxime and ceftazidime contain bulky oxyimino group at the C7 position of cephalosporin nucleus. After clinical use, however, novel β-lactamases that could inactivate even the oxyimino β-lactams appeared. For example, the chromosomal class C β-lactamase that hydrolyzes the above oxyimino β-lactams has been isolated from the Gram-negative bacteria, *Enterobacter cloacae* strain GC1 (Nukaga et al., 1995).

Clinically, class A and C β-lactamase are the most commonly encountered of the four classes. However, class C β-lactamases are more problematic than class A enzymes. Class C β-lactamases can confer resistance to cephamycins (cefoxitin and cefotetan), penicillins, cephalosporins and β-lactam/β-lactamase inhibitor combinations and are not significantly inhibited by clinically used β-lactamase inhibitor such as clavulanic acid. In contrast, Class A β-lactamases are not able to confer resistance to cephamycins and the enzymes are generally susceptible to inhibition by clavulanic acid.

Class C β-lactamases are typically synthesized by the Gram-negative bacteria and are mainly chromosomal. Recently, plasmid-encoded class C β-lactamases have been reported in several bacteria species (Lee et al., 2002). Plasmid-encoded class C β-lactamases pose more problems since they are transmissible to other bacterial species and are often expressed in a large amount (Marchese et al., 1998).

CMY-1 is the first plasmidic class C β-lactamase to be identified. CMY-10 is a variant of the above CMY-1 with a point mutation at position 346 from Asn to Ile. CMY-1 and CMY-10 display the characteristics of extended-spectrum β-lactamase (ESBLs) (Lee et al., 2003; Horii et al., 1993). The above CMY-10 enzyme is able to hydrolyze cefoxitin and cefotetan as well as penicillins, the third-generation cephalosporins, and monobactams (Lee et al., 2003; Bauernfeind et al., 1989). The high sequence identity between plasmidic β-lactamase and chromosomal lactamase clearly defines the origin of the above plasmidic enzymes. Namely, MIR-1, plasmidic β-lactamase, shows over 90% sequence identity to a chromosomal enzyme AmpC from *Enterobacter cloacae*. P99 is not ESBL, but is wild type of GC1. In the case of CMY-1 and CMY-10, however, the root is obscure since there is no closely related chromosomal class C enzyme.

Structural information on class C β-lactamase is very restricted. All available structures have been determined using chromosomal β-lactamase (Crichlow et al., 1999; Lobkovsky et al., 1993; Oefner et al., 1990; Usher et al., 1998). Thus, the structure of CMY-1 and CMY-10 will open new opportunities for structural comparison between chromosomal and plasmidic class C β-lactamases and for the design of new antibiotics that can escape hydrolysis by plasmidic class C ESBLs.

With considering the above described state, therefore, it is found the CMY-10 gene present in the plasmid isolated from *Enterobacter aerogenes* has been over-expressed in *E. coli*, followed purification and crystallization of CMY-10 according to the present invention. It is also obtained X-ray diffraction data for CMY-10 crystal and determined a three-dimensional structure of the CMY-10 molecule using the above data.

DISCLOSURE OF INVENTION

Technical Problem

The present invention is to allow using CMY-10, plasmidic class C β-lactamase, to develop new antibiotics that can prevent resistant bacteria from emerging by escaping hydrolysis by the above β-lactamase with determination of a three-dimensional structure of CMY-10 molecule from *Enterobacter aerogenes*.

TECHNICAL SOLUTION

To achieve the above objection, the present invention provides a method for crystallizing a CMY-10 being a class C β-lactamase with extended-substrate spectrum, a crystal of CMY-10, and a crystal structure of CMY-10.

The present invention will be explained in details hereinafter.

First, a method for crystallizing a CMY-10 is provided. This method is characterized in that it consists of (1) a step providing a purified CMY-10 protein; (2) a step crystallizing a purified CMY-10 protein with Microbatch crystallization method at 298K setting using precipitating agent containing 18% (w/v) polyethylene glycol 8000, 0.1 M sodium cacodylate (pH6.5) and 0.2 M zinc acetate dehydrate (condition No. 45 of Crystal Screen™ from Hampton Research); and (3) an analyzing step using a X-ray crystallography to obtain a three-dimensional structure of the above crystallized CMY-10 protein.

At this time, in the above step (1), it is used as PCR template a plasmid pYMG-1 containing bla$_{CMY-10}$ gene encoding β-lactamase produced by *Enterobacter aerogenes* which shows resistance to penicillins, three-generation cephalosporins, and monobactams as well as cefoxitin and cefotetan and is isolated at Kosin university gospel hospital, Korea in 1998. The used primer is N-NdeIF and G-XhoIB. The above two primers contain recognition sequences for NdeI (N-NdeIF) and XhoI (G-XhoIB) at each end. A method of Lee et al. is used for PCR amplification using DNA thermal cycler (mod 2400; Perkin-Elmer Getus, Norwalk, Conn., USA). PCR product of desired size 1179 bp is confirmed through an agarose gel electrophoresis. PCR product digested by NdeI/XhoI is ligated at pET-26b(+) vector (Novagen, Wisconsin, Wis., USA) digested with NdeI/XhoI. The hybrid plasmid is designated as pYMG1001. To amplify signal peptide (SP) portion fused with promoter site of pYMG1001 and His$_{11}$ (11-histidine), pYMG1001 is used as PCR template, and UP-26b-BglII and Sp-HIS as primer, thereby PCR product of HIS-CMY-SP being obtained. To amplify CMY-10 gene fused with enterokinase recognition site, pYMG-1 is used as PCR template and, EK-CMY and the above C-XhoIB as primer, thereby PCR product of EK-CMY being obtained. Ligation between blunt ends of the above PCR products, HIS-CMY-SP and EK-CMY, is carried out. Ligation product digested with BglII/XhoI is ligated at pET-26b(+) vector (Novagen, Wisconsin, Wis., USA) digested with BglII/XhoI. In order to over-express the above His$_{11}$-bla$_{CMY-10}$, the above recombinant plasmid DNA(pET-26b/His$_{11}$-b/a$_{CMY-10}$) is transformed to *Escherichia coli* strain BL21(DE3), and IPTG (isopropyl-1-thio-β-galactopyranoside) is added to induce an expression with a large amount of CMY-10 in culture broth of the above transformed cell, followed centrifugation of the above cell and re-suspension using 20 mM sodium phosphate buffer (pH 7.0, ice-cold phase). DNase I (100 ug/mL) and 1 mM PMSF (phenylmethyl sulfonyl fluoride) is added to the above suspension solution. After lysis of the above cell, a crude lysate is centrifuged again, a clarified supernatant is loaded His-Bind column (Novagen, Wisconsin, Wis., USA) equilibrated with a binding buffer (20 mM sodium phosphate, 10 mM imidazole, and 500 mM NaCl pH 7.9). And then, His$_{11}$ tag is removed from His$_{11}$-CMY-10 by enterokinase. The resulting product is desalted and concentrated with Fast Desalting column (Amersham Biosciences, UK) and then loaded to Mono S column (Amersham Biosciences, UK) equilibrated previously with 10 mM sodium phosphate buffer (pH 7.0). The nucleotide sequence of the CMY-10 isolated and purified by the above procedure is presented as SEQ ID NO: 1, and registered at GenBank with registration No. AF357598.

Next, a crystallization of CMY-10 protein in the above step (2) can be carried out by the Microbatch crystallization method at 298K set up or the hanging-drop vapor-diffusing method at a plate for culturing 24-well tissue (Supercon, South Korea), and it is obtained with a crystal of 0.3 mm size using a precipitating agent containing 18% (w/v) polyethylene glycol 8000, 0.1 M sodium cacodylate (pH 6.5), and 0.2 M zinc acetate dehydrate (condition No. 45 of Crystal Screen™ from Hampton Research). Lastly, a step analyzing a three-dimensional structure of CMY-10 protein crystal using an X-ray crystallography in the above step (3) can be carried out as following. Namely, it can be determined by obtaining an X-ray diffraction data from a cold substance of CMY-10 protein crystal, calculating an electric density from the above data and using a well-known computer program for modeling the protein. In the present invention, it is processed with a CNS program base on an X-ray diffraction data collected at 1.55 Å resolution.

The present invention provides a crystal of CMY-10 protein crystallized according to the above method.

The amino acid sequence of CMY-10 crystal according to the present invention is presented as SEQ ID NO: 2, and its space group is P2$_1$. The crystal of CMY-10 protein has unit cell parameters, a=49.70, b=59.51, c=63.75 Å and β=102.57°, and one CMY-10 molecule is included in asymmetric unit of the crystal.

The present invention also provides three-dimensional structure of CMY-10 protein crystallized according to the above method.

A ribbon diagram of three-dimensional structure of CMY-10 protein is consisted of α-domain and α/β-domain. The α-domain has three α-helices and loops. The α/β domain folds as an eight stranded antiparallel β-sheet with eight α-helices and three β-strands (β3, β4, and β7) packed on both faces of the sheet, and with two β-strands (β5 and β6) on one edge (α-helix: 11; β-strand: 13). An active site is located at a center, the upper active site is R1 site and the lower active site is R2 site. The R1 site is a space formed by flexible part of Ω loop positioned at the upper left side, Gln121 loop positioned at the most left side among α-domain and defining the edges of the active site, and β11 strand positioned at the most right side among α/β-domain and defining the edges of the active site. The R2 site is a space formed by α10, α11 helix, and Tyr151 loop positioned at the lower site. Unlike CMY-10, P99 has not extended-substrate spectrum due to its characteristic which is unable to hydrolyze third-generation cephalosporins. With comparing C$_α$ backbone diagram of P99 (representing a 40.16% sequence identity to CMY-10) with C$_α$ backbone diagram of CMY-10, the distance between α10 and adjacent α11 of R2 is extended to 2 Å due to deletion of amino acid sequence (PPA) presenting at from 303 position to 305 position in P99, and the distance between Gln121 loop and β11 strand of R1 is extended to 1 Å because residues 83-106 in the helical domain form solvent exposed loops that display the large structural deviation. The sequence difference between CMY-10 and P99 β-lactamase in this loop region is 68%. The extension of the above active site, R1 and R2 site, allows to bind a bulky oxyimino group presented at C7 position of nucleus of ceftazidime (a third-generation cephalosporin) at an active site of CMY-10, thereby CMY-10 hydrolyzing ceftazidime. With viewing a surface diagram which is a real feature of CMY-10, CMY-10 shows extended-substrate spectrum by binding with third-generation cephalosporins (ceftazidime) due to the above two extended sites able to receive oxyimino group of ceftazidime, and this phenomenon is new characteristic that only CMY-10 has. The three-dimensional structural atomic coordinates of the above CMY-10 is deposited to Protein Data Bank (PDB) with deposition No. 1ZKJ on May 3, 2005.

DESCRIPTION OF DRAWINGS

The patent or application file contains at least one drawing executed in color. Copies of this patent or patent application publication with color drawing(s) will be provided by the Office upon request and payment of the necessary fee.

Other objects and aspects of the present invention will become apparent from the following description of embodiments with reference to the accompanying drawing in which.

BEST MODE

Figure 1:
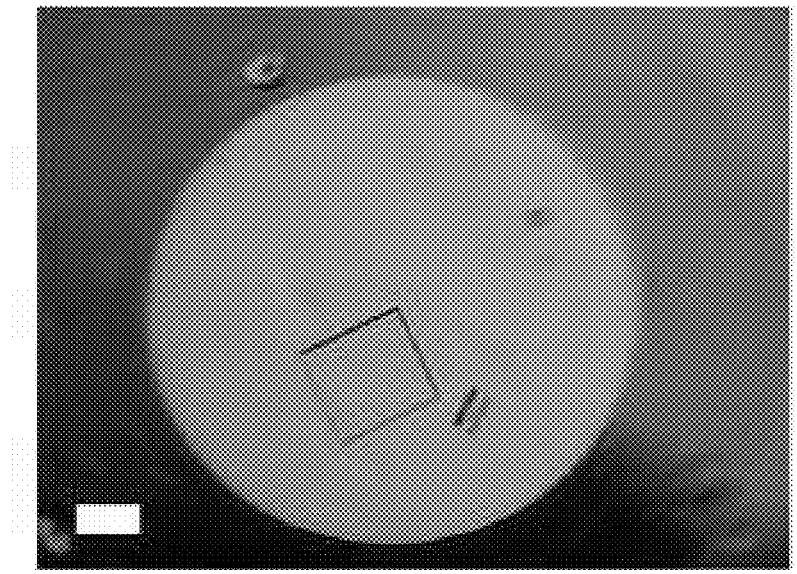
FIG. 1 is a photograph of CMY-10 crystal from *Enterobacter aerogenes*, which is crystallized according to the present invention.
Figure 2:
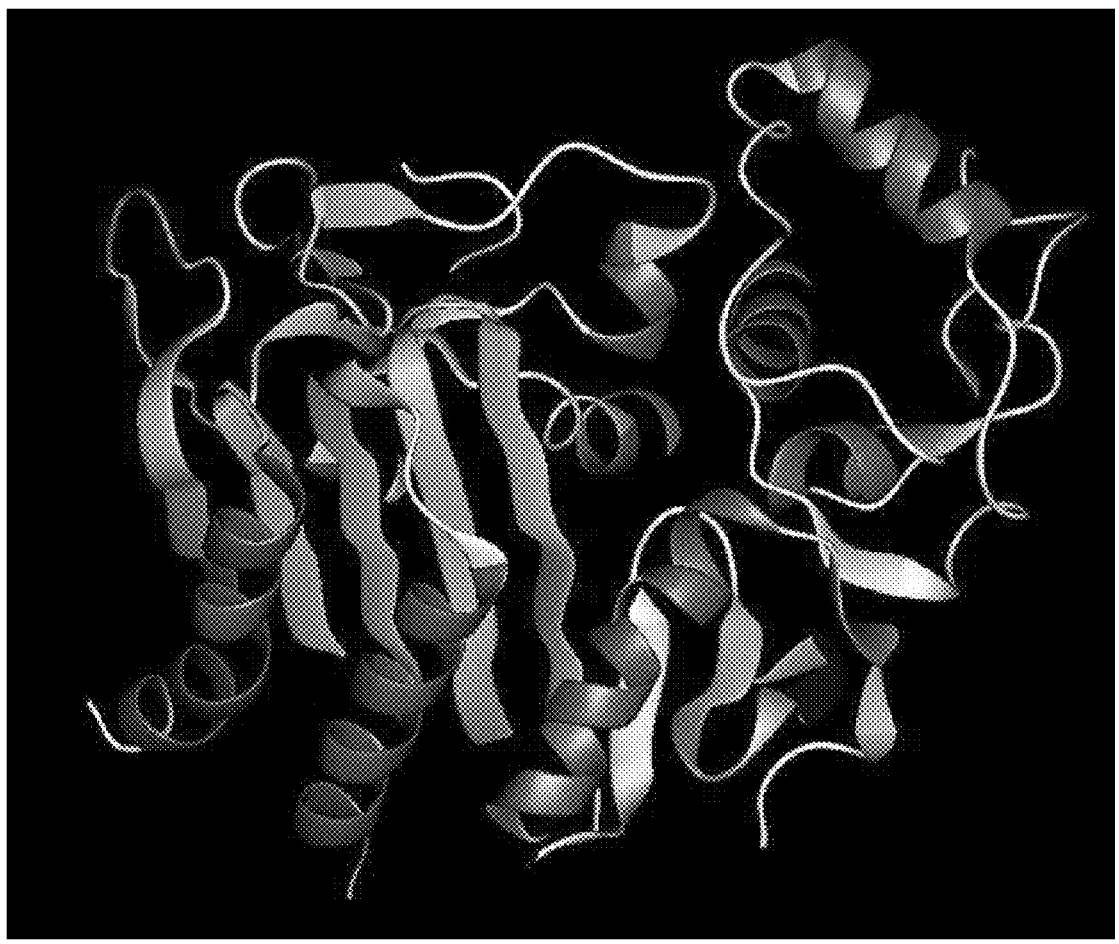
FIG. 2 shows three-dimensional molecular structure of CMY-10 from *Enterobacter aerogenes* by X-ray crystallography according to the present invention with ribbon diagram, the right of the above diagram is α-domain of CMY-10, the left is α/β-domain, and the central pouch shape is an active site, respectively. α-Helix is represented with blue color, and β-sheet is represented with yellow color.
Figure 3:
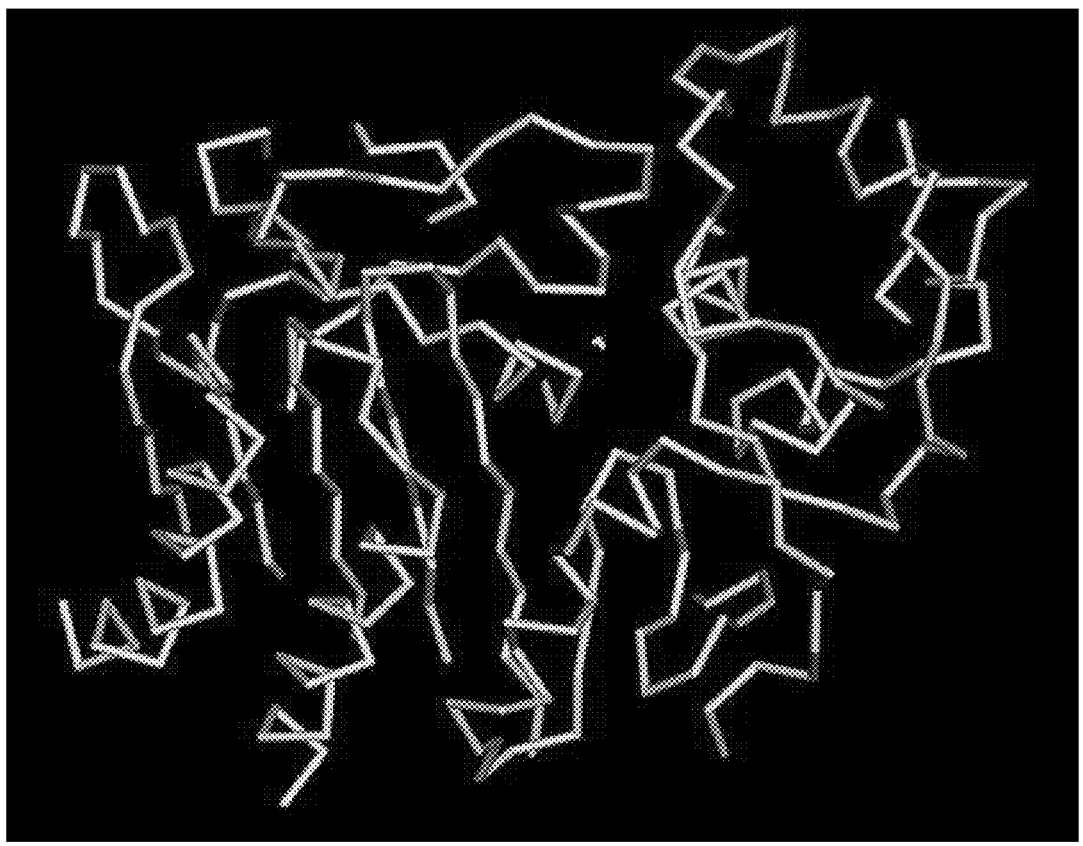
FIG. 3 is $C_\alpha$ backbone diagram showing a position of α-domain (the right), α/β-domain (the left), and an active site (the central pouch shape) of CMY-10 from *Enterobacter aerogenes* according to the present invention.
Figure 4:
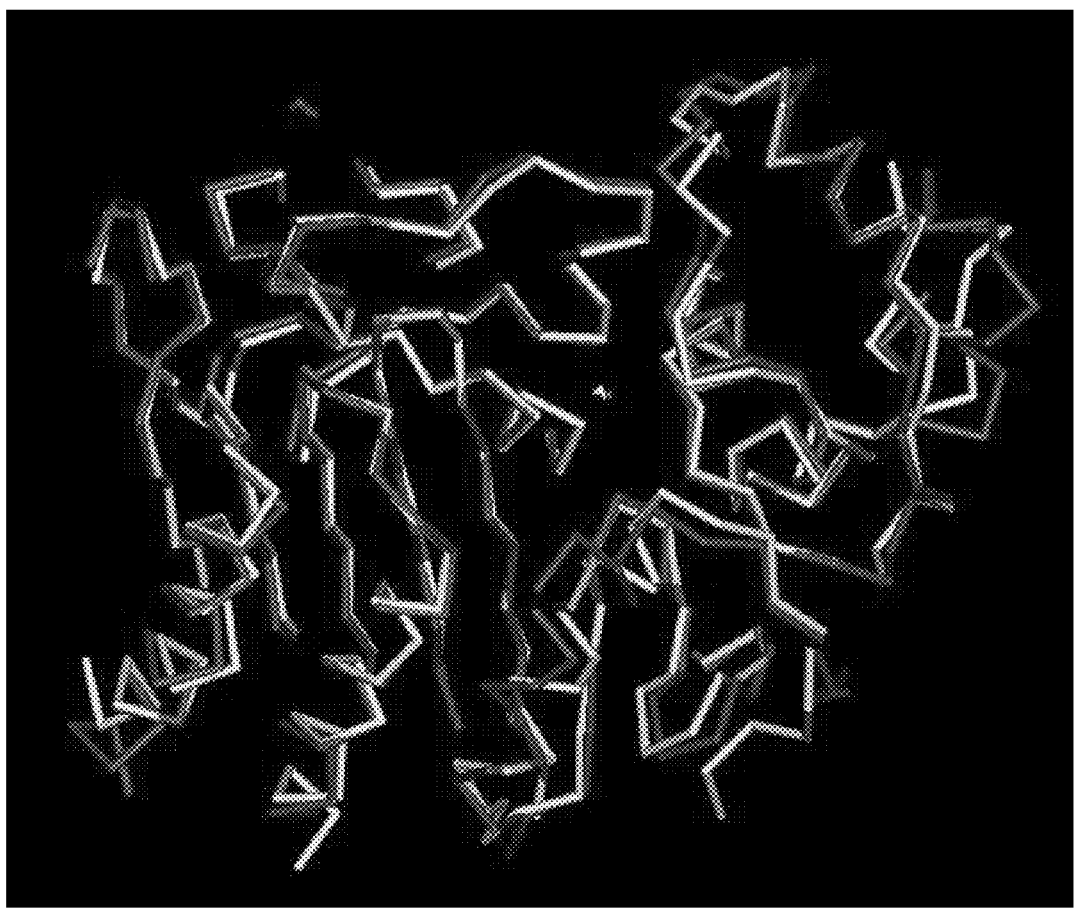
FIG. 4 is $C_\alpha$ backbone diagram showing a position of α-domain (the right), α/β-domain (the left), and an active site (the central pouch shape) of CMY-10 (yellow) from *Enterobacter aerogenes* and P99 (Red; PDB file 1BLS; representing a 40.16% sequence identity to CMY-10) from *Enterobacter cloacae* according to the present invention.
Figure 5:
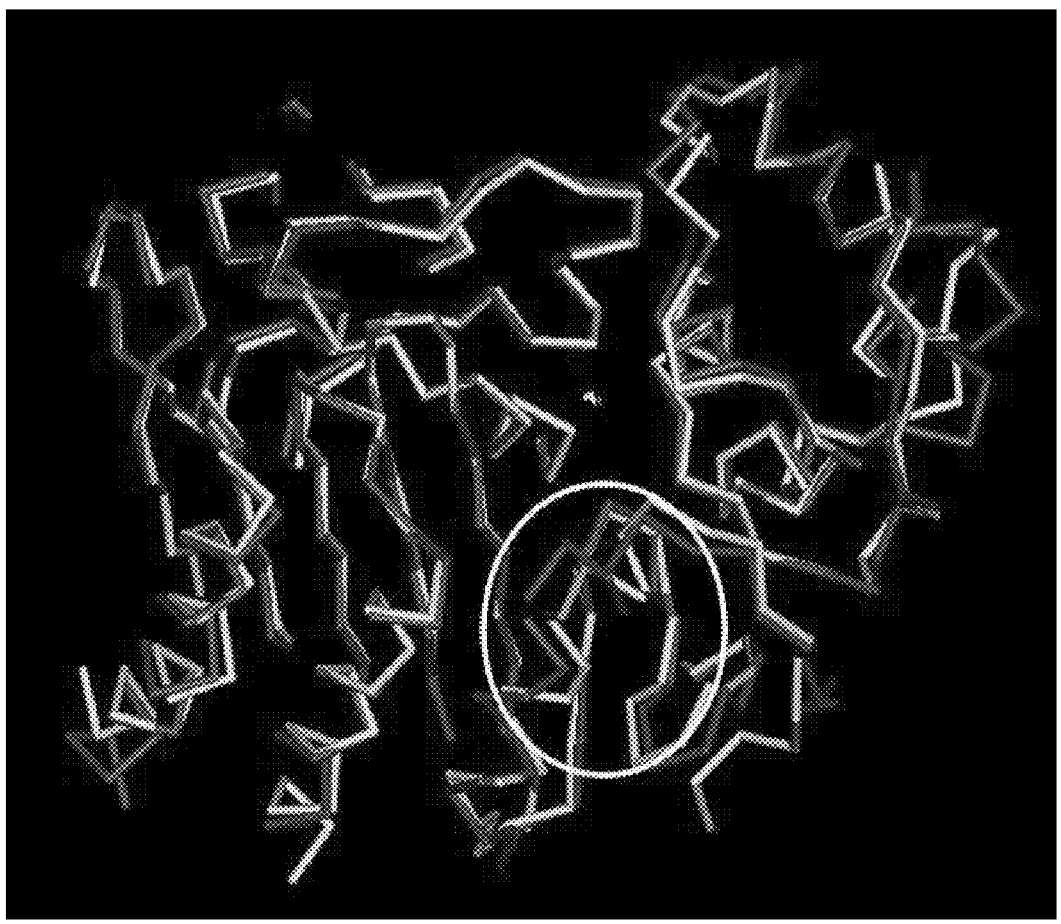
FIG. 5 is $C_\alpha$ backbone diagram of CMY-10 (yellow) and P99 (Red; PDB file 1BLS; representing a 40.16% sequence identity to CMY-10), showing the first widening position (being indicated with lower white circle, R2 active site being extended to 2 Å) of R2 active site (the central pouch shape) of CMY-10 from *Enterobacter aerogenes* by deletion of amino acid sequence (PPA) being presented at position 303 to position 305 in P99 according to the present invention.
Figure 6:
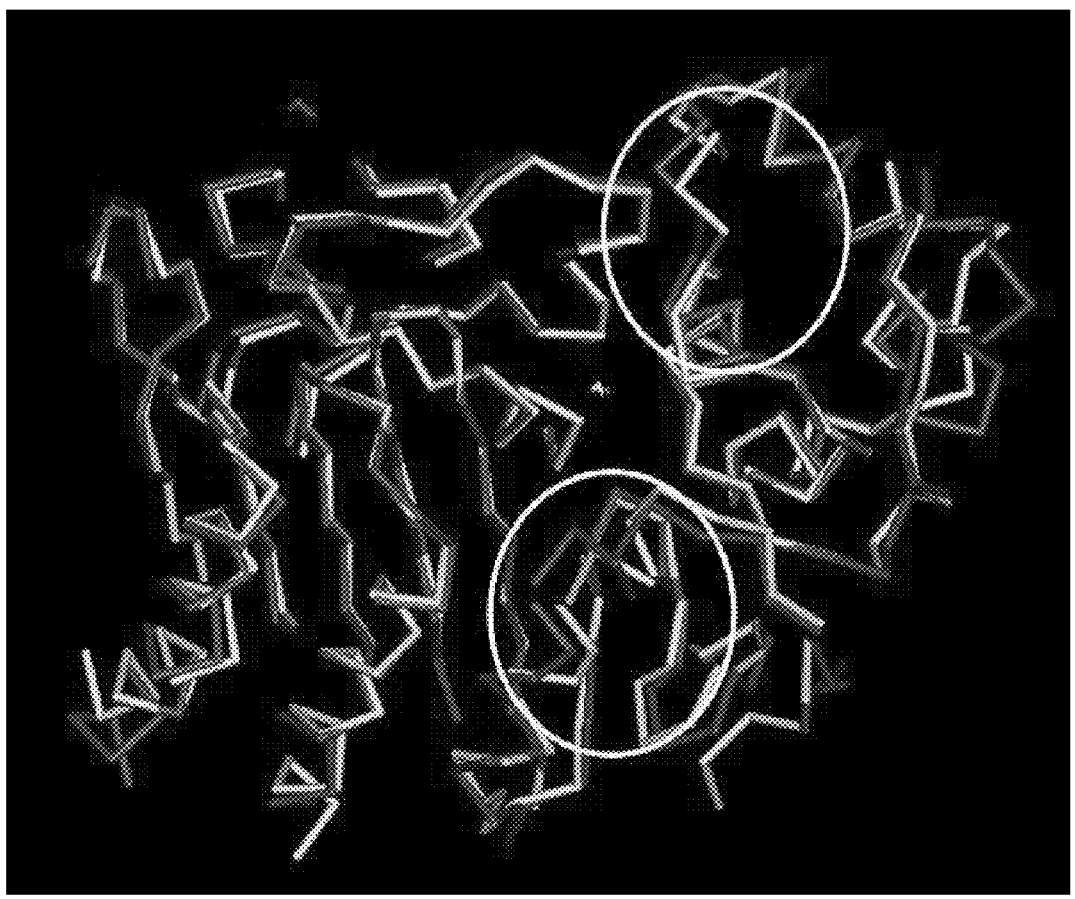
FIG. 6 is $C_\alpha$ backbone diagram of CMY-10 (yellow) and P99 (Red; PDB file 1BLS; representing a 40.16% sequence identity to CMY-10), showing the second widening position (being indicated with upper white circle, R1 active site being extended to 1 Å) of R1 active site (the central pouch shape) of CMY-10 from *Enterobacter aerogenes* by difference of amino acid residues from 83 to 106 between CMY-10 and P99 according to the present invention.
Figure 7:
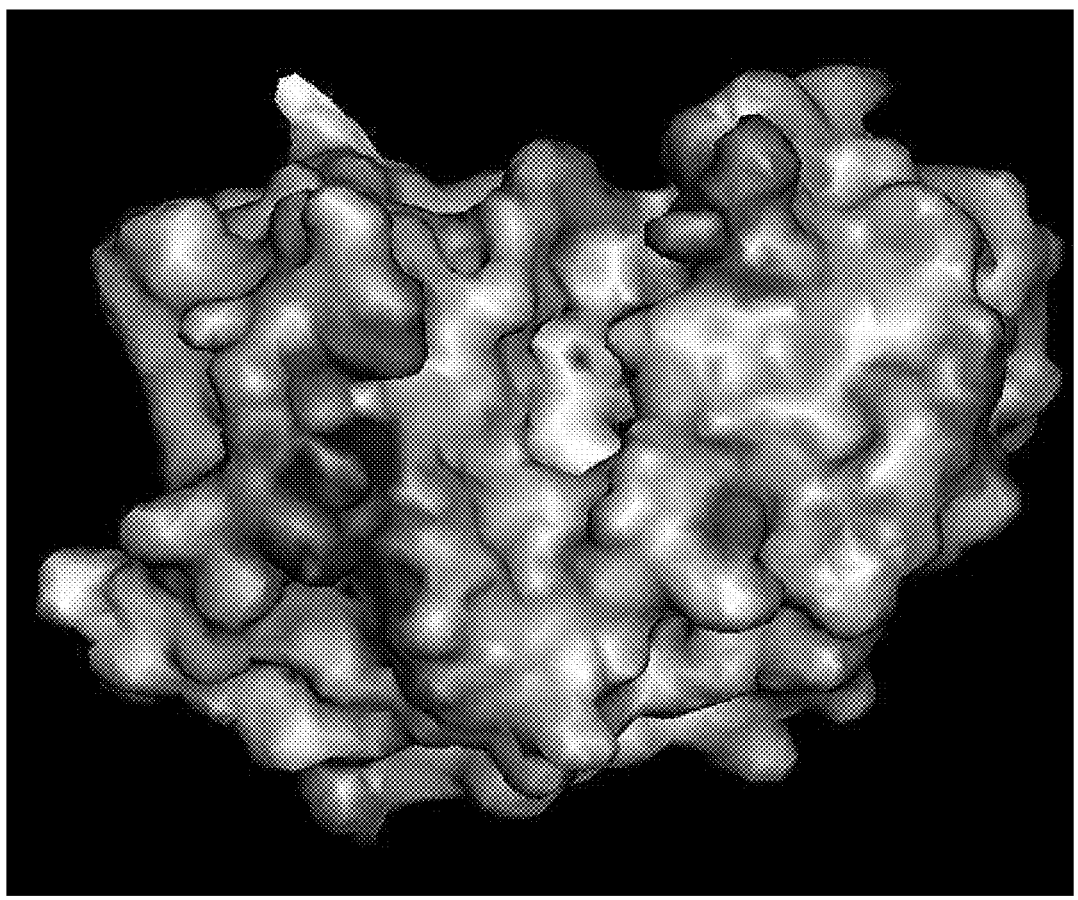
FIG. 7 is surface diagram showing a position of α-domain, α/β-domain, and an active site (the central pouch shape) of CMY-10 from *Enterobacter aerogenes* according to the present invention.
Figure 8:
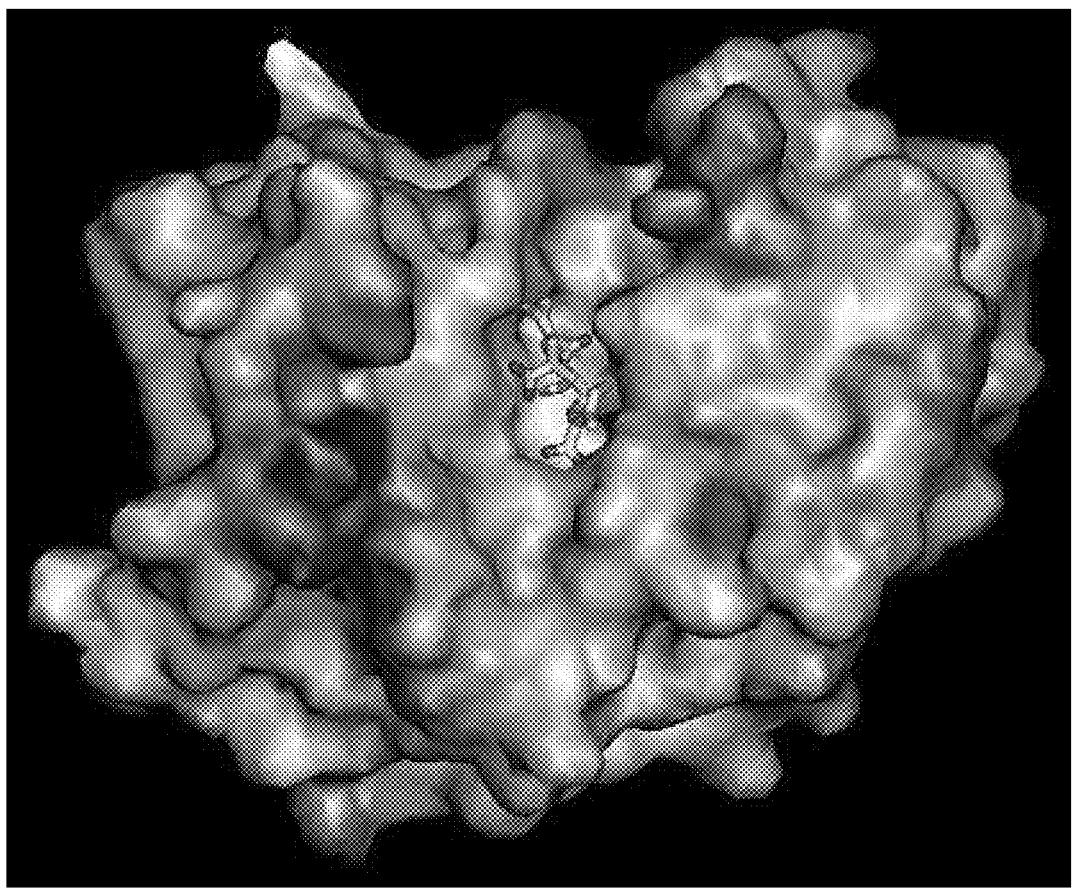
FIG. 8 is surface diagram of CMY-10 from *Enterobacter aerogenes* according to the present invention, showing extended-substrate spectrum by binding with third-generation cephalosporins (ceftazidime; central compound) due to two extended sites able to receive oxyimino group of ceftazidime and shown at FIG. 6 and FIG. 7.

A greater understanding of the present invention and its concomitant advantages will be obtained by referring to the following Example and Comparative example provided, but it is not to limit the scope of the present invention.

Example 1

Overexpression and Purification of CMY-10

To express CMY-10 as a histidine-tagged fusion form, the plasmid pYMG-1 (Lee et al., 2003) is used as PCR template and the plasmid contains $bla_{CMY-10}$ gene encoding β-lactamase produced by *Enterobacter aerogenes* which shows resistance to penicillins, three-generation cephalosporins, and monobactams as well as cefoxitin and cefotetan and is isolated at Kosin university gospel hospital, Korea in 1998. The used primer is N-NdeIF (5'-GTAGAGCATATGGAA-GAAGGAGAATGGATGGTGTGG-3' (SEQ ID NO: 3), containing NdeI recognition site shown in a bold-type) and G-XhoIB (5'-GAATGTCTCGAGGT-GTTTGTTTGAAGGGGGGAAG-3' (SEQ ID NO: 4), containing XhoI recognition site shown in a bold-type). Two primers contain recognition sequences (bold-type) for NdeI (N-NdeIF) and XhoI (G-XhoIB) at each end. A method of Lee et al. is used for PCR amplification using DNA thermal cycler (mod 2400; Perkin-Elmer Getus, Norwalk, Conn., USA). PCR product of desired size 1179 bp is confirmed through an agarose gel electrophoresis. PCR product digested by NdeI/XhoI is ligated at pET-26b(+) vector (Novagen, Wisconsin, Wis., USA) digested with NdeI/XhoI. The formed plasmid is named as pYMG1001. To amplify signal peptide (SP) portion fused with promoter site of pYMG1001 and $His_{11}$ (11-histidine), pYMG1001 is used as PCR template, and UP-26b-BglII (5'-GTATGATGGGATAGGGGGAAAG-3' (SEQ ID NO: 5), containing BglII recognition site derived from pET26b(+) in PCR product) and Sp-HIS (5'-GCTATGAT-GATGATGATGATGATGATGATGATGAT-GATCCGGTGAAGCCTCACCT GGATG-3' (SEQ ID NO: 6), containing $His_{11}$ site shown in a bold-type) as primer, thereby POR product of HIS-GMY-SP being obtained. To amplify CMY-10 gene fused with enterokinase recognition site, pYMG-1 is used as PCR template and, EK-CMY (5'-AGGGGGGATATGGACGACGACGA-CAAGGGTGAGGGTTGAGGGGTGGATG-3' (SEQ ID NO: 7), containing enterokinase recognition site shown in a bold-type) and the above G-XhoIB as primer, thereby PCR product of EK-CMY being obtained. Ligation between blunt ends of the above PCR products, HIS-GMY-SP and EK-CMY, is carried out. Ligation product digested with BglII/XhoI is ligated at pET-26b(+) vector (Novagen, Wisconsin, Wis., USA) digested with BglII/XhoI. The formed plasmid is named as pET-26b/$His_{11}$-$bla_{CMY-10}$. After verifying the above DNA sequence, in order to over-express the above $His_{11}$-$bla_{CMY-10}$, the above recombinant plasmid DNA is transformed into *Escherichia coli* strain BL21(DE3). The transformed cells are grown in Luria-Bertani medium (Difco) containing 50 ug/mL of kanamycin to an OD600 of 0.6 at 303K and expression of CMY-10 is induced with 0.5 mM IPTG (isopropyl-1-thio-β-galactopyranoside) for 16 h at 301K. Cells are harvested by centrifugation at 5000 g for 10 mm at 227K and re-suspended in ice-cold 20 mM sodium phosphate buffer pH 7.0. DNase I (100 ug/mL) and 1 mM PMSF (phenylmethyl sulfonyl fluoride) are added to the above suspension and cells are disrupted by sonication. The crude lysate is centrifuged at 20,000 g for 30 mm at 277K and the clarified supernatant is loaded onto a His-Bind column (Novagen, Wisconsin, Wis., USA) equilibrated with binding buffer (20 mM sodium phosphate, 10 mM imidazole, and 500 mM NaCl pH 7.9). For further purification, $His_{11}$ tag is removed from enterokinase according to the instruction of manufacturer, Novagen. The reaction mixture is desalted and concentrated with Fast Desalting column (Amersham Biosciences, UK) and then loaded onto Mono S column (Amersham Biosciences, UK) pre-equilibrated with 10 mM sodium phosphate buffer (pH 7.0). The soluble form of CMY-10 without $His_{11}$ tag is obtained with a yield of 9.2 mg of homogeneous protein per liter of culture. The purified CMY-10 is dialyzed against 10 mM phosphate buffer and subsequently concentrated to 17 mg/mL for crystallization. Like other class C β-lactamase, the apparent molecular weight of the purified CMY-10 is estimated to be 38 kDa by SDS-PAGE.

Example 2

Microbatch Crystallization of CMY-10

Crystals of CMY-10 is obtained by the batch-crystallization method at 298K set up by using an automatic crystallization machine, IMPAX 1-5 system (Douglas Instruments Ltd, UK). 1 uL of protein solution and an equal volume of crystallization regent are pipetted under a layer of a 1:1 mixture of silicon oil and paraffin oil in 72-well plate (Nunc). Initial crystallization conditions are tested by using all the available screening kits from Hampton Research and Emerald BioStructures Inc. As a result, the crystal of 0.3 mm size is produced by using a precipitating agent containing 18% (w/v) polyethylene glycol 8000, 0.1 M sodium cacodylate (pH 6.5), and 0.2 M zinc acetate dehydrate (condition No. 45 of Crystal Screen™ from Hampton Research). The crystal of CMY-10 is shown in FIG. 1.

As a result, the crystal of CMY-10 protein is revealed to be belonged to the monoclinic space group P2$_1$ with unit-cell parameters a=49.70, b=59.51, c=63.75 Å and β=102.57°, and the crystal volume per unit molecular weight ($V_M$) is calculated to be 2.25 Å$^3$ Da$^{-1}$ with a solvent content of 44.84% (v/v) when the unit cell is assumed to contain two molecules. This corresponds to one molecule per asymmetric unit. The statistics of data collection is shown in table 1.

TABLE 1

Characteristics of CMY-10 crystal and analysis of data-collection statistics.

| Protein | CMY-10 |
| --- | --- |
| Wavelength (Å) | 1.12714 |
| Space group | P2$_1$ |
| Unit-cell parameters (Å, °) | a = 49.70, b = 59.51, c = 63.75, β = 102.57 |
| Resolution range (Å) | 20.0-1.55 |
| Completeness (>0σ) (%) | 96.6(99.6) |
| Total/unique reflections | 267900/50744 |
| $R_{sym}$†(%) | 5.8(18.1) |
| I/σ(I) | 30.77 |

†$R_{sym} = \Sigma |I_{obs} - I_{avg}|/\Sigma I_{obs}$

Example 3

Three-Dimensional Structure Determination and Refinement of CMY-10 Protein

To obtain an X-ray data from the crystal of the above CMY-10, the crystal is soaked in a cryoprotectant solution consisted of a precipitant solution containing 15% (v/v) glycerol for a while and then flash-cooled with a nitrogen gas of 100 K by using a cooler (Oxford Cryosystems, UK). Diffraction data is collected from the above cooled CMY-10 crystal by using a MacScience 2030b area detector at beamline 6B of Pohang light Source (6B, PLS), South Korea. At this time, the wavelength of synchrotron radiation is 1.12714 Å. A total of 90 frames of 20 oscillation are measured with the crystal-to-detector distance set to 300 mm.

An X-ray diffraction data is collected at 1.55 Å resolution and processed with the program CNS (Otwinowski & Minor, 1997). After the X-ray data being obtained, an electric density map is calculated from the above data and model building of CMY-10 is carried out. In a quality analysis of a model, PROCHECK (Laskowski et al., 1993) program is used, and the results show that 83.1% among 840 ordered residues are in the most favored regions, 15.2% are in additionally allowed regions, 1.1% are in generously allowed regions, and only 0.7% are in disallowed regions. FIG. 2 to FIG. 8 are drawn up by using Raster 3D (Merrit and Murphy, 1994) and Molscript (Kraulis, 1991) program.

As a result, a ribbon diagram (see FIG. 2) of three-dimensional structure of CMY-10 protein (359 amino acid residues) is consisted of α-domain (residues 83-170) and α/β-domain (residues 1-82 and 171-359). The α-domain has three α-helices and loops. The α/β domain folds as an eight stranded antiparallel β-sheet with eight α-helices and three β-strands (β3, β4, and β7) packed on both faces of the sheet, and with two β-strands (β5 and β6) on one edge (α-helix:11; β-strand: 13). An active site is located at a center, the upper active site is R1 site and the lower active site is R2 site. The R1 site is a space formed by flexible part (residues 212-226) of Ω loop positioned at the upper left side, Gln121 loop (residues 118-128) positioned at the very left side among α-domain and defining the edges of the active site, and β11 strand positioned at the very right side among α/β-domain and defining the edges of the active site. The R2 site is a space formed by α10, α11 helix and Tyr151 loop (residues 149-152) positioned at the lower site. Unlike CMY-10, P99 has not extended-substrate spectrum due to its characteristic which is unable to hydrolyze third-generation cephalosporins. With comparing $C_\alpha$ backbone diagram (see FIG. 4) of P99 (representing a 40.16% sequence identity to CMY-10) with $C_\alpha$ backbone diagram (see FIG. 3 and FIG. 4) of CMY-10, the location and geometry of catalytic residues such as Ser65, Tyr151, the nucleophile and the main chain nitrogen atoms of Ser65 and Ser315 that form the oxyanion hole, are well conserved in P99 and CMY-10. But, the distance between α10 and adjacent all of R2 is extended to 2 Å because of the deletion of amino acid sequence (PPA) presenting from 303 position to 305 position in P99 (see white circle at FIG. 5), and the distance between Gln121 loop and β11 strand of R1 is extended to 1 Å because residues 83-106 in the helical domain form solvent exposed loops that display the large structural deviation (see white circle at FIG. 6). The sequence difference between CMY-10 and P99 β-lactamase in this loop region is 68%. The extension of the above active site, R1 and R2 site, allows to bind a bulky oxyimino group presented at C7 position of nucleus of ceftazidime (a third-generation cephalosporin) at an active site of CMY-10, thereby CMY-10 hydrolyzing ceftazidime. With viewing a surface diagram (see FIG. 7) which is a real feature of CMY-10, CMY-10 shows extended-substrate spectrum by binding with third-generation cephalosporins (ceftazidime; central compound in FIG. 8) due to the above two extended sites able to receive oxyimino group of ceftazidime, and this phenomenon is new characteristic that only CMY-10 has. Extended-substrate specificity of CMY-10 is produced by a new mechanism different from that of a chromosomal β-lactamase from *E. cloacae* GC1 (representing a 39.79% sequence identity to CMY-10) whose three-dimensional structure is only known among a class C ESBL having extended-substrate specificity for third-generation cephalosporins. The insertion mutation consisting of an unusual tandem repeat of three residues (Ala208-Val209-Arg210) in Ω-loop is responsible for the extended activity of the GC1 β-lactamase, which widens the active site enough to accommodate the oxyimino group of third-generation cephalosporins (Grichlow et al., 1999). However, CMY-10 does not have such an insertion mutation, and shows the extension of R1 and R2 active site and a new three-dimensional structural specificity describing a mechanism of extended-substrate spectrum for third-generation cephalosporins. The three-dimensional structural atomic coordinates of the above CMY-10 is deposited to Protein Data Bank (PDB with deposition No. 1ZKJ on May 3, 2005.

INDUSTRIAL AVAILABILITY

As described in detail through the above example, the present invention relates to a method for crystallizing a CMY- 10 being a β-lactamase with extended-substrate spectrum, a crystal of CMY-10, and a crystal structure of CMY-10. With utilization of three-dimensional structure of CMY-10 protein as the above description, it is possible to develop novel antibiotics or inhibitors being capable of preventing an emergence of resistance bacteria appeared by plasmidic class C β-lactamases having extended-substrate specificity, therefore the present invention is very useful in medical industry.

---

The invention claimed is:

1. A crystal of CMY-10 protein comprising and space group P2$_1$ the amino acid sequence set forth in SEQ ID NO: 2, the crystal having unit cell parameters of a=49.70 Å, b=59.51 Å, c=63.75 Å and β=102.57°.

* * * * *